United States Patent [19]

Doll et al.

[11] Patent Number: 4,971,972

[45] Date of Patent: Nov. 20, 1990

[54] PHOSPHODIESTERASE INHIBITORS HAVING AN OPTIONALLY SUBSTITUTED PURINE DERIVATIVE PORTION AND A BENZO- OR CYCLOPENTA-FURAN PORTION

[75] Inventors: Ronald J. Doll, Maplewood; Deen Tulshian, Rockaway; Charles V. Magatti, Verona, all of N.J.

[73] Assignee: Schering Corporation, Kenilworth, N.J.

[21] Appl. No.: 327,638

[22] Filed: Mar. 23, 1989

[51] Int. Cl.$^5$ .................. A61K 31/52; C07D 473/14; C07D 473/18
[52] U.S. Cl. ............................. 514/265; 514/266; 544/265; 544/276; 544/277
[58] Field of Search ................ 544/277, 276, 265; 514/265, 266

[56] References Cited

U.S. PATENT DOCUMENTS

| | | | |
|---|---|---|---|
| 4,460,765 | 7/1984 | Naito et al. | 536/26 |
| 4,634,706 | 1/1987 | Kaneko et al. | 514/262 |
| 4,822,879 | 4/1989 | Nakagawa et al. | 544/277 |

FOREIGN PATENT DOCUMENTS

| | | |
|---|---|---|
| 44527 | 1/1982 | European Pat. Off. . |
| 162715 | 11/1985 | European Pat. Off. . |
| 214708 | 3/1987 | European Pat. Off. . |
| 143557 | 6/1987 | European Pat. Off. . |
| 60-149394 | 8/1985 | Japan . |
| 61-100593 | 5/1986 | Japan . |

OTHER PUBLICATIONS

F. Nakagawa et al., J. Antibiotics, 38, 7 (1985) pp. 823–829.

S. Takahashi et al., J. Antibiotics, 38, 7 (1985) pp. 830–834.

Marquez, et al., "Medicinal Research Reviews", vol. 6, No. 1, John Wiley & Sons, Inc. (1986) pp. 1–16 and 36–40.

Primary Examiner—Diana Rivers
Attorney, Agent, or Firm—Anita W. Magatti; James R. Nelson; Stephen I. Miller

[57] ABSTRACT

Antihypertensive phosphodiesterase inhibitors having an optionally substituted purine derivative portion and a benzo- or cyclopenta-furan derivative portion are disclosed.

11 Claims, No Drawings

PHOSPHODIESTERASE INHIBITORS HAVING AN OPTIONALLY SUBSTITUTED PURINE DERIVATIVE PORTION AND A BENZO- OR CYCLOPENTA-FURAN PORTION

SUMMARY

The present invention relates to nucleoside-type compounds having an optionally substituted purine derivative as the base joined to a benzo- or cyclopentafuran derivative. Said compounds are useful as phosphodiesterase inhibitors, in particular as antihypertensives.

The present invention also relates to pharmaceutical compositions comprising said nucleoside-type compounds and to a method of treating hypertension comprising administering said compound or composition to a mammal in need of such treatment.

BACKGROUND

Cyclic guanosine monophosphate (cGMP) is known to be an important physiological mediator of vasorelaxation. A major process in vascular smooth muscle contraction is hydrolysis of cGMP by calcium-calmodulin dependent phosphodiesterase (Ca CaM PDE). Since Ca CaM PDE is selective for cGMP, selective inhibition of this enzyme should elevate cGMP levels in vascular smooth muscle and induce vasorelaxation.

Griseolic acid, disclosed in U.S. Pat. No. 4,460,765, is a nucleoside-type compound having an adenine base and a bicyclic sugar moiety and has a structure similar to adenosine 3',5'-cyclic monophosphate (cAMP). cAMP is known to be a mediator of a large number of hormones and griseolic acid similarly appears to inhibit a large variety of phosphodiesterases (PDEs).

DETAILED DESCRIPTION

Compounds of the invention are represented by the formula

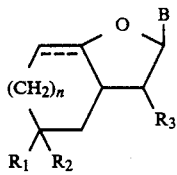     I wherein $R^1$ and $R^2$ are independently H or $-(CH_2)_mCO_2R_4$, provided that $R_1$ and $R_2$ are not both hydrogen;

$R_3$ is hydrogen or OH;

$R_4$ is hydrogen or lower alkyl;

n is 0 or 1;

m is 0–4;

the dotted line represents an optional double bond;

B is

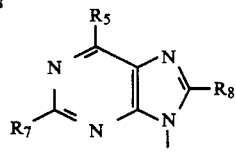

or

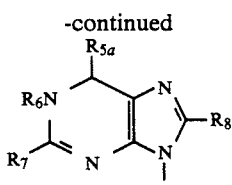

$R_5$ is $-OH$ or $-NH_2$; $R_{5a}$ is $=O$ or $=NH$;

$R_6$ is hydrogen, lower alkyl or aryl;

$R_7$ is hydrogen, amino, lower alkylamino, arylamino, lower alkylcarbonylamino, heteroaryl or heteroaryl substituted by 1–3 substituents independently selected from lower alkyl, amino, hydroxy, halogeno, thio, alkylthio and arylthio;

$R_8$ is hydrogen, halogeno, lower alkyl or aryl; and the pharmaceutically acceptable esters or salts thereof.

Those skilled in the art will recognize that tautomerism exists in group B, i.e.,

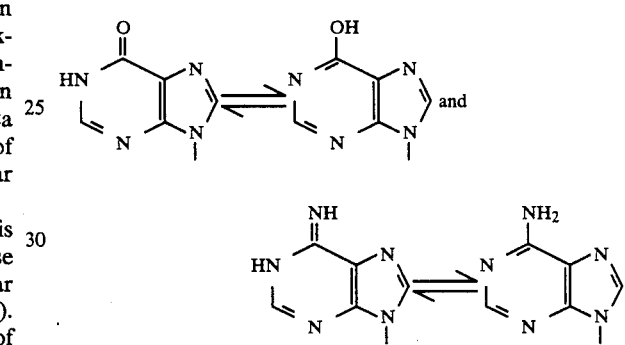

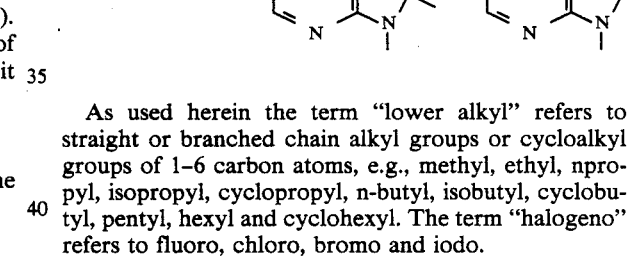

As used herein the term "lower alkyl" refers to straight or branched chain alkyl groups or cycloalkyl groups of 1-6 carbon atoms, e.g., methyl, ethyl, npropyl, isopropyl, cyclopropyl, n-butyl, isobutyl, cyclobutyl, pentyl, hexyl and cyclohexyl. The term "halogeno" refers to fluoro, chloro, bromo and iodo.

The term "aryl" refers to phenyl or substituted phenyl wherein the substituents are as defined in $R_7$. The term "heteroaryl" refers to aromatic 4–7 membered rings comprising 1–3 heteroatoms independently selected from oxygen, nitrogen and sulfur. Examples of heteroaryl groups are pyridyl, pyrimidyl, thienyl, furanyl. All positional isomers, e.g. 2-, 3- and 4-pyridyl are included.

Preferred compounds are those wherein B is guanine (i.e., $R_5$ is OH, $R_8$ is hydrogen and $R_7$ is amino). Also preferred are compounds of formula I wherein $R_3$ is OH. A preferred $R_1$ group is $-CO_2R_4$. A preferred $R_2$ group is $-CH_2CO_2R_4$.

Typical preferred compounds are those listed in the following table:

| n | double bond | $R_1$ | $R_2$ | $R^3$ | B |
|---|---|---|---|---|---|
| 1 | absent | COOH | CH$_2$COOH | OH | guanino |
| 1 | absent | COOCH$_3$ | CH$_2$COOCH$_3$ | OH | guanino |
| 1 | present | COOH | CH$_2$COOH | OH | guanino |
| 1 | present | COOCH$_3$ | CH$_2$COOCH$_3$ | OH | guanino |
| 0 | absent | COOH | CH$_2$COOH | H | guanino |
| 0 | absent | COOCH$_3$ | CH$_2$COOCH$_3$ | OH | guanino |
| 0 | present | COOH | CH$_2$COOH | OH | guanino |
| 0 | present | COOCH$_3$ | CH$_2$COOCH$_3$ | OH | guanino |

For those compounds wherein the optional double bond is not present, both the cis and trans isomers are preferred.

The compounds of the invention form salts with various inorganic and organic acids and bases. Such salts include alkali metal salts, e.g. sodium and potassium salts, and alkaline earth metal salts, e.g. calcium and magnesium salts. Salts with organic bases also may be prepared, e.g., N-methylglucamine, lysine and arginine salts. Those compounds with a basic substituent e.g., wherein $R_9$ is hydrogen, may form salts with organic and inorganic acids, e.g., HCl, HBr, $H_2SO_4$, methanesulfonic acid, toluenesulfonic acid, maleic acid, fumaric acid and camphorsulfonic acid. The non-toxic pharmaceutically acceptable salts are preferred.

The salts may be formed by conventional means, as by reacting the free acid or base forms of the product with one or more equivalents of the appropriate base or acid in a solvent or medium in which the salt is insoluble, or in a solvent such as water which is then removed in vacuo, or by exchanging the cations of an existing salt for another cation on a suitable ion exchange resin.

The compounds of the present invention have a number of asymmetric carbon atoms in their molecules and consequentially various stereoisomers can exist. All isomers and racemates are contemplated in the present invention. Examples of stereoisomers of compounds of formula I are as follows:

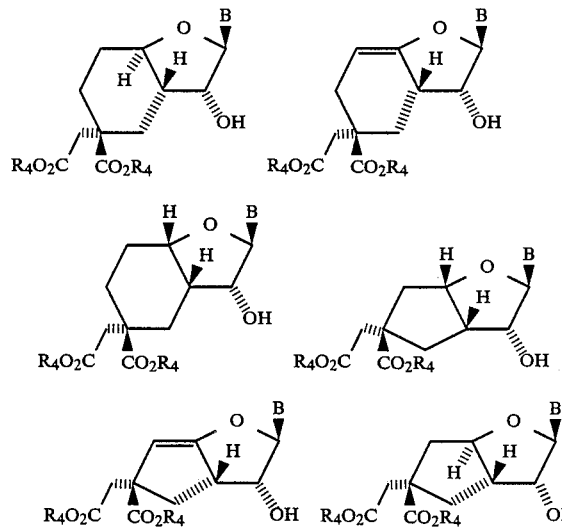

Compounds wherein n is 1 are hexa- or octahydrobenzofurans and compounds wherein n is 0 are tetrahydro- or hexahydro-2H-cyclopenta[b]furans. Stereochemistry is designated by α or β.

Compounds of the present invention are made by methods well known in the art. For example, a compound of formula II is reacted with a compound of formula III (or the corresponding tautomeric compound, e.g. wherein $R_{5a}$ is =O):

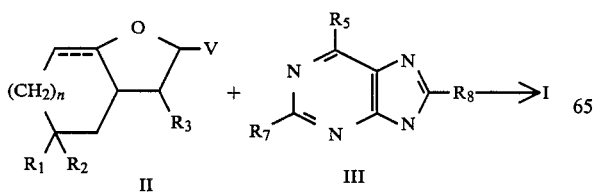

wherein V is a leaving group such as acetoxy, although other suitable leaving groups can be used. $R_1$, $R_2$, $R_3$ (when it is hydroxy) and $R_5$–$R_8$ may be protected by suitable protecting groups, e.g., an acetyl group may be used to protect $R_3$, and when III is guanino, i.e. when $R_5$ is OH and $R_7$ is $NH_2$, the amino group is preferably protected by an acetyl and a trimethylsilyl (TMS) group and the OH is preferably protected by a TMS group. Such persilylation of the compound of formula III increases solubility.

The reaction of II and III is carried out at elevated temperatures (e.g., 60° C.) in an inert solvent such as 1,2-dichloroethane.

Alternatively, a compound of formula IV

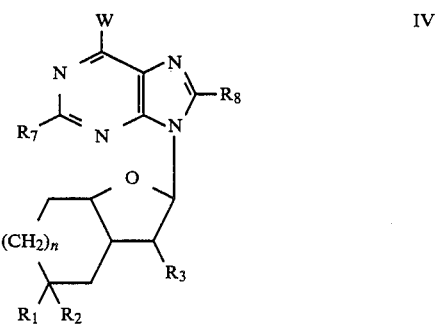

may be treated with a base, then an acid, to obtain a compound of formula I. In formula IV, W is chlorine, bromine, OH or $NH_2$ wherein the OH and $NH_2$ are preferably protected by suitable protecting groups as defined above, and wherein the remaining substitutents are as defined above.

The present invention also is directed toward intermediate compounds of the formulae II and IV wherein the substituents are as defined above.

Compounds of formula II can be prepared by several methods, depending on the value of n and the presence or absence of the double bond. The following reaction scheme 1 shows a typical procedure for compounds wherein n is 1.

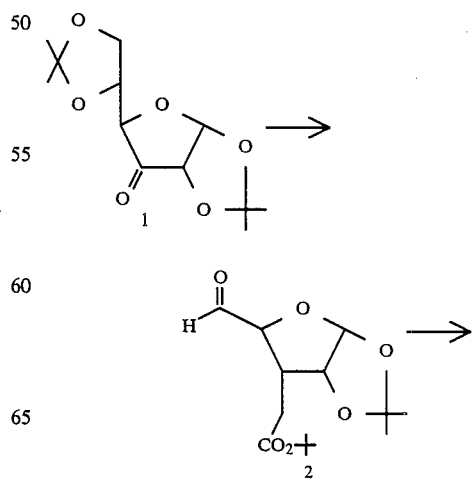

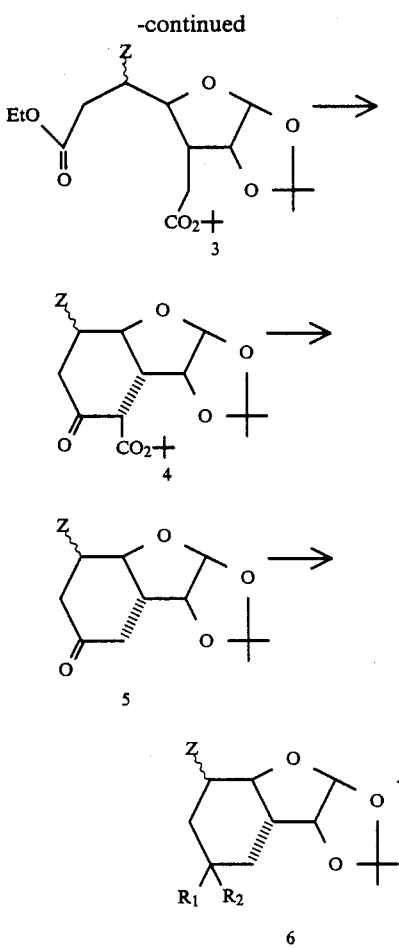

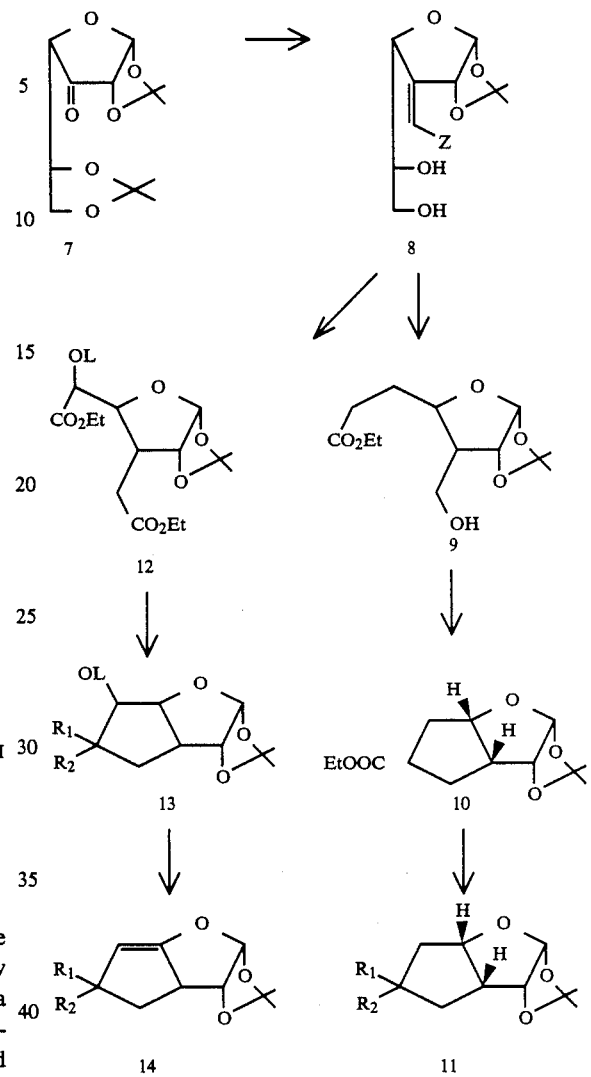

Known keto sugar 1 is easily converted to aldehyde ester 2. The aldehyde and ester functional groups allow the construction of a six membered ring by use of a Reformatsky reaction, giving 3, followed by a Dieckmann cyclization to give 4. Ester hydrolysis followed by decarboxylation gives ketone 5. The ketone function of 5 is used to introduce the carboxy functions $R_1$ and $R_2$ into 6 by various methods known in the art. One example is a Knovenagel condensation with ethyl cyanoacetate followed by a Michael reaction with cyanide and then hydrolysis to the diacid. Removal of the isopropylidine followed by diacetylation gives a compound of formula II. For intermediate 3, Z is initially OH. This hydroxy can be protected, as with a benzyl ether, and later used to produce the claimed compounds containing a double bond. Hydrogenation of these compounds containing a double bond gives claimed compounds with a cis ring fusion. Alternatively, hydroxy-containing intermediate 3 (Z=OH) can be deoxygenated to an intermediate 3 wherein Z is hydrogen. This can be done by various methods known in the art. One method is to convert the hydroxy to a halide (e.g., 3 wherein Z is iodo), and then to replace the halide with hydrogen. This gives compounds of formula I with a trans ring fusion.

Compounds of formula II, where n=0 can be prepared using following reaction scheme 2.

Known keto sugar 7 can be condensed with an appropriate Wittig reagent and selective hydrolysis of 5,6-O-isopropylidene gives 8. Compound 8 can be modified depending upon the stereochemistry of the ring junction and the absence or presence of a double bond in the desired compound of formula II. For compounds containing a double bond and trans ring junction, 8 can be converted to 12 via a selective protection of the primary hydroxyl, then protection of the secondary hydroxyl with a suitable group "L" as shown in scheme 2, followed by deprotection and oxidation of the primary hydroxyl group. Compound 12 is then converted to 13 using the reaction sequence described for transforming compound 3 into compound 6 in scheme 1. Elimination of OL will give the olefinic compound and catalytic hydrogenation of 14 leads to the trans ring configuration. For compounds of formula II containing a cis ring junction, diol 8 is cleaved using periodate, a Wittig reaction is carried out on the resulting aldehyde, and reduction gives 9. The hydroxy group of 9 is then converted to a leaving group such as tosylate or mesylate, which is then displaced in presence of a base to give 10. The ester functionality of compound 10 is then used to introduce the $R_2$ functionality to obtain compound 11.

Following are examples of the preparation of compounds of this invention.

PREPARATION 1

3-Deoxy-3-C-(Carbo-tert-Butoxymethyl)-1,2-O-Isopropylidene-α-D-Ribo-Pentadialdo-1-4-Furanose Step 1: Dissolve 15g of tert-butyl(triphenylphosphoramylidene)acetate and 11 g of 1,2,5,6-di-O-isopropylidine-α-D-ribo-3-hexofuranosulose in 80 ml of benzene. Reflux for 4 hr. and concentrate in vacuo. Triturate the residue and filter. Mix the solid with 100 ml of hot hexane and filter. Repeat the hexane wash three times to obtain a white product.

Step 2: Dissolve 8.0g of the product from Step 1 in 200 ml of ethanol (EtOH) containing 1g of 10% palladium on carbon (Pd/C). Hydrogenate this mixture at 60 psi. using a Parr Instruments hydrogenator. After 10 hr., filter the catalyst and concentrate the filtrate in vacuo. The resulting oil crystallizes upon standing. M.p 74°–75° C. Elemental analysis: theoretical value for $C_{18}H_{30}O_7$ is C=60.32, H=8.44; value found is C=60.25, H=8.69.

Step 3: Dissolve 7.0g of the product from Step 2 in a mixture of 45 ml of methanol (MeOH) and 45 ml of 0.8% aqueous sulfuric acid ($H_2SO_4$). Stir this solution for 30 hr., then neutralize with barium carbonate. Filter the mixture and concentrate the filtrate in vacuo. Dissolve the residue in 200 ml of dichloromethane ($CH_2Cl_2$) and wash with 100 ml of water. Separate the organic layer and dry over magnesium sulfate ($MgSO_4$). Filter and concentrate in vacuo to obtain a colorless oil. MS =318. Elemental analysis: theoretical value for $C_{15}H_{26}O_7$ is C=55.04, H=8.25; value found is C=54.56, H=7.99.

Step 4: Suspend 5.4g of the product from step 3 in 100 ml of water. Stir vigorously and add 3.6g of sodium periodate in portions. During this addition, keep the pH at 7 by adding 0.1N sodium hydroxide (NaOH). Stir the mixture for 1 hr., then add 300 ml of chloroform ($CHCl_3$) Separate the organic layer and wash successively with saturated sodium chloride (NaCl) solution and saturated sodium bicarbonate ($NaHCO_3$) solution. Dry the organic layer over $MgSO_4$ and concentrate in vacuo to give 3-deoxy-3-C-(carbo-tert-butoxy-methyl)-1,2-0-isopropylidine-α-D-ribo-pentadialdo-1-4-furanose as a waxy solid, m.p. 64°–65° C, $[\alpha]D^{26} = +87.8°$ (C=1 $CHCl_3$) Elemental analysis: theoretical value for $C_{14}H_{24}O_6$ is C=58.32, H=8.39; value found is C=58.54, H=8.30.

EXAMPLE I

2βR-(Guanin-9-yl)-3α-Hydroxy-5β-Carboxy-3aα,7aα-Octahydrobenzofuran-5α-Acetic Acid Step 1: Dissolve 4g of the product of Preparation 1 in 26 ml of dry benzene containing 4g of ethyl bromoacetate and 1.4g of zinc powder. Heat to 60° C. under nitrogen, then add 2.6 ml of dry tetrahydrofuran (THF). After the vigorous reaction has subsided (about 15 min.), cool the reaction to room temperature. Add 100 ml of ethyl acetate (EtOAc) and add saturated NaCl solution dropwise until a granular precipitate results. Filter and wash the filtrate with saturated NaCl solution. Dry the organic layer over $MgSO_4$ and concentrate in vacuo. Chromatograph the residue on a silica gel column using EtOAc:hexane (20:80) to give a mixture of the two diastereomers, $R_f$=3.8 and 3.2 on silica gel thin layer chromatography (TLC) using EtOAc:hexane (25:75) as eluent.

Step 2: Dissolve 2.5 g of the product from Step 1, 6.5g of triphenylphosphine, 1.7 g of imidazole and 3 g of iodine in 50 ml of toluene. Reflux for three hours or until reaction is complete by silica gel TLC using EtOAc:hexane (25:75) as eluent. Cool to room temperature and stir with 50 ml of saturated $NaHCO_3$ solution. Wash the organic layer with 15 ml aqueous sodium thiosulfate solution and 15 ml of saturated NaCl solution. Dry the organic layer over $MgSO_4$ and concentrate in vacuo. Chromatograph the residue on silica gel using EtOAc:hexane (10:90) as eluent to obtain a colorless oil.

Step 3: Dissolve 5 g of the product from Step 2 in 500 ml of benzene containing 3 ml of tri-n-butyl-tinhydride. Photolize with a sun lamp until the reaction is complete as determined by silica gel TlC using EtOAc:hexane (10:90) as eluent. Add 50 ml of water and wash with saturated NaCl solution. Dry the organic layer over $MgSO_4$ and concentrate in vacuo. Chromatograph the residue on silica gel using EtOAc:hexane (10:90) to obtain a colorless oil.

Step 4: Dissolve 3 g of the product from Step 3 in 150 ml of THF containing 0.05 ml of EtOH and 0.5 g of sodium hydride. Reflux until the reaction is complete as determined by TLC using EtOAc:hexane (10:90) as eluent. Cool to room temperature. Add 100 ml of water and 200 ml of ethyl ether ($Et_2O$). Dry the organic layer over $MgSO_4$ and concentrate in vacuo to obtain a colorless oil.

Step 5: Dissolve 5 g of the product from Step 4 in 7 ml of water and 500 mg of dimethylsulfoxide (DMSO). Cool to room temperature and add 500 ml of EtOAc and 500 ml $Et_2O$. Wash with 200 ml of saturated NaCl solution. Dry the organic layer over $MgSO_4$ and concentrate in vacuo to obtain an oil.

Step 6: Treat the product of Step 5 (1 mmole) with cyano-ethyl acetate (1.2 eq), acetic acid (HOAc) (0.8 eq) and ammonium acetate (0.1 to 0.3 mmole) in benzene (15 ml) at reflux for 2 hr. Dilute the resultant reaction mixture with benzene (50 ml). Wash the solution with saturated $NaHCO_3$ solution, dry the organic layer over $MgSO_4$ and concentrate in vacuo.

Step 7: Treat the product of Step 6 (1.0 mmol) in 10 ml aqueous EtOH with potassium cyanide (2.0 mmol) at room temperature for 0.5 hr. Adjust the resultant solution to pH 5 with 1HCl, evaporate in vacuo, dissolve the resultant residue in THF (20 ml) and cool in an ice bath. Add diazomethane until the reaction is complete as monitored by TLC. Decompose excess diazomethane with HOAc and concentrate in vacuo. Dissolve the residue in pyridine (10 ml) and acetic anhydride (7 ml) and stir at room temperature for 18 hrs. Concentrate in vacuo, dissolve the residue in EtOAc (100 ml), wash with 50 ml of $NaHCO_3$ solution, dry the organic layer over $MgSO_4$ and concentrate in vacuo.

Step 8: Dissolve the product of Step 7 (1.0 mmol) and persilylated $N^2$-acetyl guanine (1.30 mmol) in dry 1,2-dichloroethane. Add trimethylsilyltrifluoromethane sulfonate and reflux the solution until the reaction is complete as monitored by TLC. Cool the reaction mixture, wash with a cold solution of saturated $NaHCO_3$, dry the organic layer over $MgSO_4$ and concentrate in vacuo. Chromatograph on silica gel using EtOAc:hexane to separate isomers.

Step 9: Stir the product of Step 8 (1.0 mmol) and NaOH (5.0 mmole) in aqueous EtOH (15 ml) for 4 hrs.

Neutralize with 1N HCl and evaporate the solvent to reduce the volume to half. Adjust the pH to 4, charge the solution to a CHP$_{20}$P gel (Mitsubishi Chemical Industries) column and elute with water, followed by 50% acetone in water. Collect the desired fractions and evaporate in vacuo to obtain the title compound.

EXAMPLE II

2βR-(Guanin-9-yl)-3α-Hydroxy-5β-Carbomethoxy-3aβ,7aα-Octahydrobenzofuran-5α-Acetic Acid Methyl Ester Dissolve the product of Example I (1.0 mmol) in a mixture of dimethylformamide (DMF):THF (10:90) (25 ml) containing 1 ml of N,O-bis(trimethylsilyl)acetamide. Add diazomethane until the reaction is complete. Decompose the excess diazomethane with HOAc and concentrate in vacuo. Dissolve the residue in EtOAc, wash with saturated NaHCO3 solution, dry the organic layer over MgSO$_4$ and concentrate in vacuo to obtain the title compound.

EXAMPLE III

2βR-(Guanin-9-yl)-3α-Hydroxy-5β-Carboxy-2,3,3aα,4,5,6-Hexahdyrobenzofuran-5α-Acetic Acid Step 1: Dissolve 1.0 mmol of the product of Example I, Step 1 in 30 ml of DMSO containing sodium hydride (1.5 mmole). Stir at 25° C. for 30 min., then add benzyl chloride (3.0 mmole). Stir for 1 hr, then pour into 200 ml of ice water and extract with ether. Dry the ether layer over MgSO$_4$ and concentrate in vacuo.

Step 2: Treat 0.1 mmole of the product of Step 1 as in Example I, Steps 4–7.

Step 3: Dissolve the product of Step 2 (1.0 mmole) in 100 ml of EtOH containing 0.5 g of 10% Pd/C. Hydrogenate at 60 psi for 10 hr., filter and concentrate in vacuo to obtain a residue.

Step 4: Dissolve the product of Step 3(1.0 mmol) in 5 ml of pyridine and cool to 0° C. Add methane-sulfonyl chloride (1.5 mmol) and allow the mixture to warm to 25° C. Stir for 10 hr., then pour into 20 ml of ice water and extract with ether (200 ml). Wash the ether layer with 20 ml of 10% HCl followed by NaHCO3 solution. Dry the organic layer over MgSO$_4$ and concentrate in vacuo to obtain a residue.

Step 5: Suspend di-O-nitrophenyl diselenide (1.6 mmol) in 5 ml of EtOH. Add sodium borohydride (3.0 mmol). Stir for 30 min. at room temperature, then cool to 0° C. Add a solution of the product of Step 4 (1.0 mmol) in 5 ml of EtOH and stir the mixture for 18 hrs. at room temperature. Add 200 ml of ether and wash with 2×50 ml portions of water. Dry the organic layer over MgSO$_4$ and concentrate in vacuo. Dissolve the resulting residue in 10 ml of THF, cool to 0° C. and add 0.5 ml of 50% hydrogen peroxide. Stir the mixture at 25° C. for 18 hrs., add 200 ml of ether and wash with water followed by brine. Dry the organic layer over MgSO$_4$ and concentrate in vacuo. Chromatograph the resultant residue on silica gel using ether:hexane, collect the desired fraction and evaporate the solvent in vacuo to obtain a residue.

Step 6: React the product of Step 5 (1.0 mmol) as in Steps 8 and 9 of Example I to obtain the title compound.

EXAMPLE IV

2βR-(Guanin-9-yl)-3α-Hydroxy-5β-Carbomethoxy-2,3,3aβ4,5,6-Hexahydrobenzofuran-5α-Acetic Acid Methyl Ester Follow the procedure of Example II, replacing the product of Example I with the product of Example III to obtain the title compound.

EXAMPLE V

2βR-(Guanin-9-yl)-3α-Hydroxy-5β-Carboxy-3aβ-7aβ-Octahydrobenzofuran-5α-Acetic Acid Step 1: Dissolve the product of Example III, Step 5 (1.0 mmol) in 500 ml of EtOH containing 0.5 g of 10% Pd/C. Hydrogenate the mixture at 60 psi using a Parr Instruments hydrogenator. After 10 hrs., filter the catalyst and concentrate the filtrate in vacuo.

Step 2: Treat the product of Step 1 (1.0 mmole) as described in Steps 8 to 9 of Example I to obtain the title compound.

EXAMPLE VI

2βR-(Guanin-9-yl)-3α-Hydroxy-5β-Carbomethoxy-3aβ,7aβ-Octahydrobenzofuran-5α-Acetic Acid Methyl Ester Using the procedure of Example II, replace the product of Example I with the product of Example V to obtain the title compound.

EXAMPLE VII

2βR-(Guanin-9-yl)-3α-Hydroxy-5β-Carboxy-3aβ,6aβ-Hexahydro-2H-Cyclopenta[b]furan-5α-Acetic Acid Step 1: Condense 1,2:5,6-di-O-isopropylidene-α-D-xylohexofuranose-3-ulose (1.0 mmole) with benzoxy methyltriphenylphosphonium bromide (1.3 mmol) in the presence of n-butyl lithium (1.3 mmol) in dry THF (50.0 ml) at −40° C. After completion of the reaction, add a few drops of a saturated solution of ammonium chloride and evaporate the solvent. Column chromatograph the residue on silica gel.

Step 2: Treat the product of Step 1 (1.0 mmole) in CH$_3$OH (10 ml) with 0.7 M H$_2$SO$_4$ (1.0 ml) until the reaction is complete. Neutralize the mixture with NaHCO$_3$ and extract with CH$_2$Cl$_2$ (3×100 mL). Dry the organic layer over MgSO$_4$ and evaporate the solvent. Dissolve the resultant residue in 20 ml of MeOH, treat it with a solution of sodium-metaperiodate (1.20 mole in water), reduce the volume of the reaction mixture to half and extract with EtOAc (2×100 mL). Dry the organic layer over MgSO$_4$ and evaporate the solvent.

Step 3: Add carboethoxy-methylene-triphenyl phosphorane (2.0 mmole) to a solution of the product of Step 2 (1.5 mmole in 30 mL of acetonitrile) and reflux until the reaction is complete. Remove the solvent and chromatograph the resultant residue on a silica gel column to obtain a residue.

Step 4: Hydrogenate a solution of the product of Step 3 (1.0 mmole) in absolute EtOH (50 mL) with Pd/C until the reaction is complete. Filter the resultant solution and remove the solvent under reduced pressure.

Step 5: Treat the product of Step 4 (1.0 mmole) in 30.0 mL dry pyridine with p-toluene sulfonyl chloride (1.20 mmole) at room temperature until reaction is complete. Pour the reaction mixture over ice, extract the product with CH$_2$Cl$_2$ (200 mL), dry over MgSO$_4$ and evaporate the solvent.

Step 6: Treat a solution of the product of Step 5 (1.0 mmole) in THF with sodium hydride. Reflux the resultant mixture until reaction is complete. Cool the reaction mixture, add MeOH (2.0 mL) and remove the solvent. Extract the residue with $CH_2Cl_2$, wash the organic layer wtih water, dry over $MgSO_4$ and evaporate the solvent. Chromatograph the resultant residue on a silica gel column, collecting the desired fraction to obtain a residue.

Step 7: Cool a solution of the product of Step 6 (1.0 mmole) in THF (20 mL) to $-78°$ C., add lithium diisopropylamide (2.2 mmol) and keep at $-78°$ C. for half an hour. Add iodoethyl acetate (2.2 mmol) and slowly warm the reaction mixture. Add a solution of saturated ammonium chloride, concentrate, and dissolve the resultant residue in $CH_2Cl_2$. Wash with water, dry the organic layer over $MgSO_4$ and concentrate. Chromatograph the resultant residue on a silica gel column.

Step 8: Cool a solution of the product of Step 7 (1.0 mmol) in HOAc (10.0 mL) and acetic anhydride (7.0 mL). Add a catalytic amount of $H_2SO_4$ and stir at room temperature for 1 day. Pour the resultant mixture into ice water, extract with $CH_2Cl_2$ (3×75 mL), wash with saturated $NaHCO_3$ solution, then water, dry the organic layer over $MgSO_4$ and evaporate the solvent.

Step 9: Treat the product of Step 8 as described in Steps 8 and 9 of Example I.

EXAMPLE VIII

2$\beta$R-(Guanin-9-yl)-3$\alpha$-Hydroxy-5$\beta$-Carbomethoxy-3a$\beta$,6a$\beta$-Hexahydro-2H-Cyclopenta[b]furan-2$\alpha$-Acetic Acid Methyl Ester Using the process of Example II, replace the product of Example I with the product of Example VII to obtain the title compound.

EXAMPLE IX

2$\beta$R-(Guanin-9-yl)-3$\alpha$-Hydroxy-5$\beta$-Carboxy-3,3a$\alpha$,4,5-Tetrahydro-2H-Cyclopenta[b]furan-5$\alpha$-Acetic Acid Step 1: Condense 1,2:5,6-di-0-isopropylidine-a-D-xylohexofuranose-3-ulose (1.0 mmol) with diethyl (carboethoxymethyl)phosphonate (1.2 mmol) in the presence of sodium hydride (1.2 mmoles) at 0° C. in 1,2-dimethoxy ethane. Allow the mixture to warm to room temperature and maintain at room temperature until the reaction is complete. Dilute the reaction mixture with ice-water and extract with $Et_2O$. Dry the organic layer over $MgSO_4$. Column chromatograph the resultant residue on silica gel to obtain a residue.

Step 2: Hydrogenate the cis and trans mixture of the product of Step 1 in EtOH in the presence of 10% Pd/C at room temperature, filter and evaporate the solvent.

Step 3: Dissolve the product of Step 2 (1.0 mmol) in MeOH (20 mL), add 0.7M $H_2SO_4$ (1.0 mL) and keep the reaction mixture at room temperature for 6-10 hrs. Neutralize the mixture by adding solid sodium bicarbonate and extract with $CH_2Cl_2$ (4×50 mL). Dry the organic layer over $MgSO_4$ and evaporate the solvent.

Step 4: Treat the product of Step 3 (1.0 mmol) with t-butyldimethylsilylchloride (1.2 mmole) and imidazole (1.2 mmole) in $CH_2Cl_2$ (50 mL). After completion of the reaction as monitored by TLC, dilute the reaction mixture with $CH_2Cl_2$ (50 mL), wash with water, dry the organic layer and evaporate the solvent. Dissolve the residue in THF and treat the solution with sodium hydride (1.2 eq). Add benzyl bromide (1.0 eq) and stir the reaction for 6 hrs. Add methanol, evaporate the solvent, dissolve the residue in $CH_2Cl_2$ (100 mL) and wash with water. Dry the organic layer, evaporate the solvent, and azeotrope the residue with toluene. Dissolve the residue in THF and treat it with tetra-n-butyl ammonium fluoride. Remove the solvent and column chromatograph the resultant residue. Dissolve the residue in THF and treat it with tetra-n-butylammonium fluoride. Evaporate the solvent and chromatograph the residue. Dissolve the resultant product in carbon tetrachloride and treat it with ruthenium chloride and a solution of sodium-metaperiodate in water. After oxidation is complete, extract the aqueous layer with $CH_2Cl_2$, dry the organic layer and evaporate the solvent. Dissolve the residue in $Et_2O$ then treat it with diazomethane. Destroy excess diazomethane with HOAc and evaporate the solvent. Column chromatograph the residue on silica gel.

Step 5: Treat the product of Step 4 as described in Steps 4,5,6 and 7 of Example I. Hydrogenate this product in EtOH in presence of 10% Pd/C. Filter the reaction mixture and evaporate the solvent.

Step 6: Treat the product of Step 5 as described in Steps 4 and 5 of Example III.

Step 7: Treat the product of Step 6 as described in Steps 8 and 9 of Example I.

EXAMPLE X

2$\beta$R-(Guanin-9-yl)-3$\alpha$-Hydroxy-5$\beta$-Carbomethoxy-3,3a$\beta$,4,5-Tetrahydro-2H-Cyclopenta[b]furan-5$\alpha$-Acetic Acid Methyl Ester Using the process of Example II, replace the product of Example I with the product of Example IX to obtain the title compound.

EXAMPLE XI

2$\beta$R-(Guanin-9-yl)-3$\alpha$-Hydroxy-5$\beta$-Carboxy-3a$\beta$,6a$\alpha$-Hexahydro-2H-Cyclopenta[b]furan-5$\alpha$-Acetic Acid Step 1: Hydrogenate the product of Step 3 of Example IX in absolute EtOH in the presence of 10% Pd/C. Filter the resultant reaction mixture and evaporate the solvent.

Step 2: Treat the product of Step 1 as described in Step of Example VII and Steps 8-9 of Example I.

EXAMPLE XII

2$\beta$R-(Guanin-9-yl)-3$\alpha$-Hydroxy-5$\beta$-Carbomethoxy-3a$\beta$,6a$\alpha$-Hexahydro-2H-Cyclopenta[b]furan-5$\alpha$-Acetic Acid Methyl Ester Using the process of Example II, replace the product of Example I with the product of Example XI to obtain the title compound.

The compounds of this invention are useful in view of their pharmacological properties. In particular, compounds of this invention possess activity as antihypertensive agents.

The compounds of this invention can be combined with pharmaceutical carriers to prepare well known pharmaceutical dosage forms suitable for oral or parenteral administration. Such pharmaceutical compositions are useful in the treatment of cardiovascular disorders and particularly mammalian hypertension.

The effective daily antihypertensive dose of the compounds of this invention will typically be in the range of about 1-50, preferably about 1-25 mg/kg mammalian weight, administered in single or divided doses. The exact dose to be administered is determined by the attending clinician and is dependent upon where the particular compound lies within the above quoted range, as well as upon the age, weight and condition of the individual.

Generally, in treating humans having hypertension, the compounds of this invention may be administered to patients in need of such treatment in a dosage range of about 10 to about 300 mg per patient generally given several (e.g., 1-4) times a day, thus giving a total daily dosage of from about 10 to about 1200 mg per day.

The compounds of the present invention are preferably administered orally, e.g., in tablets or capsule form, but may also be administered parenterally, e.g., injectable solutions or suspensions. Also contemplated are mechanical delivery systems, e.g., transdermal dosage forms.

We claim:

1. A compound having the structural formula

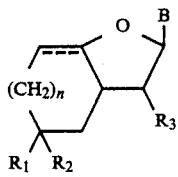

I wherein
  $R_1$ and $R_2$ are independently H or $-(CH_2)_mCO_2R_4$, provided that $R_1$ and $R_2$ are not both hydrogen;
  $R_3$ is hydrogen or OH;
  $R_4$ is hydrogen or lower alkyl;
  n is 0 or 1;
  m is 0-4;
  the dotted line represents an optional double bond;
  B is

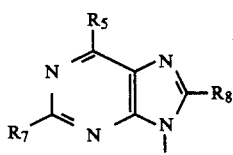

or

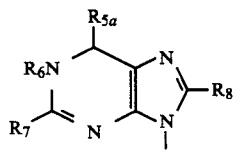

B is

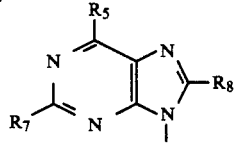

or

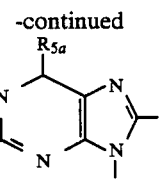

$R_5$ is $-OH$ or $-NH_2$; $R_{5a}$ is $=O$ or $=NH$;
  $R_6$ is hydrogen, lower alkyl or aryl;
  $R_7$ is hydrogen, amino, lower alkylamino, arylamino, lower alkylcarbonylamino, heteroaryl or heteroaryl substituted by 1–3 substitutents independently selected from lower alkyl, amino, hydroxy, halogeno, thio, alkylthio and arylthio, wherein the heteroaryl is selected from the group consisting of pyridyl, pyrimidyl, thienyl and furanyl;
  $R_8$ is hydrogen, halogeno, lower alkyl or aryl; and the pharmaceutically acceptable esters or salts thereof.

2. A compound of claim 1 wherein B is guanino.
3. A compound of claim 1 wherein $R_3$ is OH.
4. A compound of claim 1 wherein $R_1$ is $-CO_2R_4$.
5. A compound of claim 1 wherein $R_2$ is $-CH_2CO_2R_4$.
6. A compound of claim 1 wherein $R_1$ is $-CO_2R_4$, $R_2$ $-CH_2CO_2R_4$ and $R_4$ is hydrogen or methyl.
7. A compound of claim 6 wherein n is O.
8. A compound of claim 6 wherein n is 1.
9. A compound of claim 1 which is
  2βR-(guanin-9-yl)-3α-hydroxy-5β-carboxy-3αβ,7αα-octahydrobenzofuran-5α-acetic acid;
  2βR-(guanin-9-yl)-3α-hydroxy-5β-carbomethoxy-3αβ,-7αα-octahydrobenzofuran-5α-acetic acid methyl ester;
  2βR-(guanin-9-yl)-3α-hydroxy-5β-carboxy-2,3,3αβ,4,5,6-hexahydrobenzofuran-5α-acetic acid;
  2βR-(guanin-9-yl)-3α-hydroxy-5β-carbomethoxy2,3-,3αβ,4,5,6-hexahydrobenzofuran-5α-acetic acid methyl ester;
  2βR-(guanin-9-yl)-3α-hydroxy-5β-carboxy-3αβ-7αβ-octahydrobenzofuran-5α-acetic acid;
  2βR-(guanin-9-yl)-3α-hydroxy-5β-carbomethoxy-3αβ,-7αβ-octahydrobenzofuran-5α-acetic acid methyl ester;
  2βR-(guanin-9-yl)-3α-hydroxy-5β-carboxy-3αβ,6αβ-hexahydro-2H-cyclopenta[b]furan 5α-acetic acid;
  2βR-(guanin-9-yl)-3α-hydroxy-5β-carbomethoxy-3αβ,-6αβ-hexahydro-2H-cyclopenta[b]furan-5α-acetic acid methyl ester;
  2βR-(guanin-9-yl)-3α-hydroxy-5β-carboxy-3,3αα,4,5-tetrahydro-2H-cyclopenta[b]furan-5α-acetic acid;
  2βR-(guanin-9-yl)-3α-hydroxy-5β-carbomethoxy-3,3αα,4,5-tetrahydro-2H-cyclopenta[b]furan-5α-acetic acid methyl ester;
  2βR-(guanin-9-yl)-3α-hydroxy-5β-carboxy-3αβ,6αα-hexahydro-2H-cyclopenta[b]furan-5α-acetic acid; or
  2βR-(guanin-9-yl)-3α-hydroxy-5β-carbomethoxy-3αβ,-6αα-hexahydro-2H-cyclopenta[b]furan-5α-acetic acid methyl ester.

10. A method of treating hypertension comprising administering an antihypertensive effective amount of a compound of claim 1 to a mammal in need of such treatment.

11. A pharmaceutical composition comprising an antihypertensive-effective amount of a compound of claim 1 and a pharmaceutically acceptable carrier.

* * * * *